United States Patent [19]

Okabayashi et al.

[11] Patent Number: 4,591,575

[45] Date of Patent: May 27, 1986

[54] NOVEL CRYSTALLINE METAL OXIDE AND PROCESS FOR PRODUCTION THEREOF

[75] Inventors: Minahiro Okabayashi; Shigeki Yuasa, both of Fujisawa; Koshi Kusumoto, Kamakura, all of Japan

[73] Assignee: Tokuyama Soda Kabushiki Kaisha, Yamaguchi, Japan

[21] Appl. No.: 606,610

[22] Filed: May 3, 1984

[30] Foreign Application Priority Data

May 4, 1983 [JP] Japan .................................. 58-77502

[51] Int. Cl.$^4$ ........................... C04B 35/16; C09K 3/10
[52] U.S. Cl. ..................................... 501/154; 501/134; 501/135; 106/35
[58] Field of Search .................... 501/33, 12, 154, 134, 501/135; 106/35; 423/202

[56] References Cited

U.S. PATENT DOCUMENTS

| | | | |
|---|---|---|---|
| 2,680,677 | 6/1954 | Broge et al. | |
| 3,791,808 | 2/1974 | Thomas | 501/12 |
| 4,211,682 | 7/1980 | Suminoe et al. | 106/35 |
| 4,278,632 | 7/1981 | Yoldas | 501/12 |
| 4,308,014 | 12/1981 | Kawahara et al. | 106/35 |

OTHER PUBLICATIONS

Nogami et al, "Glass Formation Through Hydrolysis of Si(OC$_2$H$_5$)$_4$ with NH$_4$OH and HCl Solution", Journal of Non-Crystalline Solids, vol. 37 (1980), pp. 191–200.
Sanders, "High Tech Ceramics", C & EN, Washington, Jul. 9, 1984, pp. 31 and 32.
Masayuki Yamane and Takuo Kojima, Journal of Non-Crystalline Solid, 44, pp. 181–190 (1981).

Primary Examiner—William R. Dixon, Jr.
Assistant Examiner—Karl Group
Attorney, Agent, or Firm—Sherman and Shalloway

[57] ABSTRACT

A crystalline metal oxide in the form of a solid solution comprising an oxide of a metal of Group II of the periodic table, titanium oxide and silicon dioxide as main components and having main peaks at about 26.7° and about 20.9° in its Cu-Kα X-ray diffraction pattern (2θ) and a specific refractive index. The crystalline metal oxide is produced, for example, by dissolving a compound of a metal of Group II of the periodic table, a hydrolyzable organic silicon compound and a hydrolyzable titanium compound in an organic solvent, hydrolyzing said starting compounds in said solution or after said solution is added to a separately prepared solvent incapable of dissolving the reaction product, thereby to form a sol- or gel-like product, and thereafter calcining the sol- or gel-like product at a temperature and for a period of time sufficient to crystallize said product.

9 Claims, 3 Drawing Figures

NOVEL CRYSTALLINE METAL OXIDE AND PROCESS FOR PRODUCTION THEREOF

BACKGROUND OF THE INVENTION

1. Field of the Invention

This invention relates to a metal oxide solid solution comprising an oxide of a Group II metal of the periodic table, titanium oxide and silicon oxide as main components; and more specifically, to a novel crystalline metal oxide having main peaks at about 26.7° and about 20.9° in its Cu-Kα X-ray diffraction pattern (2θ) and a specific refractive index, and a process for the production thereof.

2. Description of the Prior Art

Alpha-quartz, known as one crystalline metal oxide, has been used in various applications. Artificial preparation of this quartz requires a process involving growth of crystal particles at high temperatures and pressures, and therefore, the process is too expensive to gain full industrial acceptance. It has been desired therefore to develop a technique of producing alpha-quartz under mild manufacturing conditions. To date, however, no industrial process for producing alpha-quartz under mild conditions has been established.

Although not with a view to producing alpha-quartz, Yamane et al. produced a gel composed of $SrO-SiO_2$, and found that when this transparent gel was heated at about 600° C., it became whitely turbid. They presumed this phenomenon to be due to the formation of alpha-quartz. [Journal of Non-Crystalline Solids, 44 (1981), 181-190: "Low Temperature Synthesis of Non-Crystalline Solids of the System $SrO-SiO_2$"]. The phenomenon found by Yamane et al. is interesting, but repetition of this experiment by the present inventors has shown that the white turbidity was due to the formation of cristobalite, and alpha-quartz could not be produced.

In the field of improving the hardness of synthetic resins or reinforcing them, it has recently been desired to develop inorganic compounds having superior properties which meet this purpose, particularly spherical (pearl-like), film-like or fibrous inorganic oxides. It would be especially significant to establish a technique of producing alpha-quartz having various shapes such as spheres, fibers, films, etc. industrially under mild conditions.

SUMMARY OF THE INVENTION

The present inventors have long endeavored to develop inorganic fillers for dental composite resins, and have consequently established a technique of producing a metal oxide having an X-ray diffraction pattern similar to the X-ray diffraction pattern of alpha-quartz by a combination of specific raw materials under mild conditions. This technique can give a novel metal oxide solid solution containing an oxide of a metal of Group II of the periodic table, titanium oxide and silicon oxide as main components, which is in various shapes such as a sphere, film, fiber, rod or plate and has an X-ray diffraction pattern similar to that of alpha-quartz.

It is an object of this invention therefore to provide a novel metal oxide which shows an X-ray diffraction pattern similar to that of alpha-quartz.

Another object of this invention is to provide a novel metal oxide which shows an X-ray diffraction pattern similar to that of alpha-quartz and can assume various shapes such as a sphere (pearl-like), fiber, film, rod or plate.

Still another object of this invention is to provide a process for producing the aforesaid novel metal oxide under mild conditions.

Other objects of this invention will become apparent from the following detailed description.

The novel metal oxide provided by this invention is a crystalline metal oxide in the form of a solid solution which comprises (i) an oxide of a Group II metal of the periodic table, (ii) titanium oxide and (iii) silicon oxide as main components and has main peaks at about 26.7° and about 20.9° in its Cu-Kα X-ray diffraction pattern (2θ) and a specific refractive index.

BRIEF DESCRIPTION OF THE DRAWINGS

In the drawings attached to the application for facilitating an understanding of the invention.

DETAILED DESCRIPTION OF THE INVENTION

In the crystalline metal oxide of this invention, silicon oxide, the oxide of a Group II metal and titanium oxide are present in the form of a solid solution.

The Group II metal of the periodic table may be a metal of Group IIa such as beryllium (Be), magnesium (Mg), calcium (Ca), Strontium (Sr), and barium (Ba), and a metal of Group IIb such as zinc (Zn) and cadmium (Cd), Usually, the metals of Groups IIa of the periodic table are preferred.

Since the components of the crystalline metal oxides form a solid solution, they cannot be physically separated from each other. That these components form a solid solution can be substantiated by the fact that the crystalline metal oxide has a specific refractive index, and its infrared absorption spectrum shows a peak assigned to the Ti—O—Si bond in the vicinity of 950 $cm^{-1}$.

Furthermore, X-ray diffraction analysis and differential thermal analysis show the crystalline metal oxide of this invention to be in a crystal form similar to alpha-quartz. For example, this can be determined from the fact that in its Cu-Kα X-ray diffraction pattern (2θ), the crystalline metal oxide of the invention has main peaks at about 26.7° and about 20.9°. The angles of 2θ in the Cu-Kα X-ray diffraction pattern slightly shift depending upon the proportion of the oxide of Group II metal and titanium oxide. The aforesaid similarity of the crystal form to alpha-quartz can also be demonstrated by the fact that in its differential thermal analysis, an endothermic peak showing transition between alpha-quartz and beta-quartz is observed near 570° C.

The proportion of the oxide of Group II metal and titanium oxide as components of the crystalline metal oxide of the invention affects the crystal form of the resulting crystalline metal oxide.

To obtain the crystalline metal oxide having an X-ray diffraction pattern similar to that of alpha-quartz, the proportions of each of the oxide of Group II metal and titanium oxide in the crystalline metal oxide is generally preferably 0.2 to 10 mol %, especially preferably 1 to 5 mol %. If the above proportion is smaller than the lower limit specified above, the resulting metal oxide is sometimes not crystalline. If, on the other hand, the proportion exceeds the upper limit, the X-ray diffraction pattern of the resulting crystalline metal oxide tends to show that of cristobalite or tridymite.

The proportion of the oxide of Group II metal and titanium oxide contained in the crystalline metal oxide of this invention can be determined by chemical analysis or fluorescent X-ray analysis. Since, however, the aforesaid proportion usually does not so much differ from that calculated from the ratio of the starting materials by theoretical calculation, it can be calculated from the ratio of the starting materials if the latter is known.

The crystalline metal oxide generally has a specific surface area of as low as less than 100 m$^2$/g, usually 4 to 50 m$^2$/g, because its production generally goes through a step of calcining a sol or gel. Some crystalline metal oxides in accordance with this invention have the —OH group bonded to their surface. The amount of the OH group can be determined by measurement in accordance with an alkali neutralization method. In many cases, they have 0.01 to 0.10 mmol/g of the OH group.

The specific gravity and refractive index of the crystalline metal oxide of this invention cannot be generalized because they differ depending upon the type and proportion of the oxide of Group II metal and the proportion of titanium oxide. Most generally, crystalline metal oxides in accordance with this invention have a specific gravity in the range of 2.66 to 3.12 and a refractive index of 1.53 to 1.60, but usually many of them have a specific gravity of 2.70 to 2.88 and a refractive index of 1.53 to 1.57.

The crystalline metal oxide of this invention can be obtained in various shapes such as a sphere, plate, film, fiber or rod. Or it may be irregularly shaped. When the shape is spherical, a metal oxide having a very uniform particle diameter in the range of 0.1 to 1.0 micron micrometer can be obtained. For example, there can be obtained a metal oxide in which the standard deviation (defined hereinafter) of its particle diameter distribution is 1.30 or less. In the case of spherical particles of the metal oxide, the shape, particle diameter, the particle size distribution, etc. can be measured by photographing the metal oxide under a scanning or transmission electron microscope. In the case of crystalline metal oxides of the other shapes, their shapes or sizes can be determined by observation under an electron microscope or an optical microscope, or by using a measuring instrument such as a slide caliper.

The crystalline metal oxide of this invention can be obtained in the various shapes described above. There is no particular restriction on the method of producing the crystalline metal oxide of the invention, and any method of production can be used which can give crystalline metal oxides having the aforesaid properties. The most typical method of production will be described below in detail.

According to this invention, there is provided a process for producing a crystalline metal oxide comprising an oxide of a Group II metal of the periodic table, titanium oxide and silicon oxide as main components and having main peaks at about 26.7° and about 20.9° in its Cu-Kα X-ray diffraction pattern (2θ) and a specific refractive index, which comprises dissolving a compound of a Group II metal of the periodic table, a hydrolyzable organic silicon compound and a hydrolyzable organic compound in an organic solvent, hydrolyzing said starting compounds in said solution or after said solution is added to a separately prepared solvent incapable of dissolving the reaction product, thereby to form a sol- or gel-like product, and calcining said sol- or gel-like product at a temperature and for a period of time sufficient to crystallize said product.

One starting material for producing the crystalline metal oxide of this invention is a hydrolyzable organic silicon compound. Various organic silicon compounds are known, and can be used in this invention without any particular limitation. Preferred because of ready industrial availability are, for example, alkoxysilanes of the general formula Si(OR)$_4$, and low condensation products obtained by partial hydrolysis of the alkoxysilanes. R in the above general formula is an alkyl group, preferably a lower alkyl group such as a methyl, ethyl, isopropyl or butyl group. Commerically available alkoxysilanes or low condensates may be used as such or after purification by distillation.

Another starting material for the production of the crystalline metal oxide of this invention is a hydrolyzable titanium compound. Known titanium compounds can be used without any limitation. Generally preferred are titanium alkoxide compounds of the general formula Ti(OR')$_4$ where R' is an alkyl group and compounds resulting from substitution of a carboxyl group or a beta-dicarbonyl group for one or two alkoxide groups (OR') in the above general formula. Examples of preferred titanium compounds used in this invention include Ti(O—isoC$_3$H$_7$)$_4$, Ti(O—nC$_4$H$_9$)$_4$, Ti[O—CH$_2$CH(C$_2$H$_5$)C$_4$H$_9$]$_4$, Ti(O—C$_{17}$H$_{35}$)$_4$, Ti(O—i-soC$_3$H$_7$)$_2$[CO(CH$_3$)CHCOCH$_3$]$_2$, Ti(O—nC$_4$H$_9$)$_2$[OC$_2$H$_4$N(C$_2$H$_4$OH)$_2$]$_2$, Ti(OH)$_2$[OCH(CH$_3$)COOH]$_2$, Ti[OCH$_2$CH(C$_2$H$_5$)CH(OH)C$_3$H$_7$]$_4$, and Ti(O—nC$_4$H$_9$)$_2$(OCOC$_{17}$H$_{35}$).

The other starting material for the production of the crystalline metal oxide of this invention is a compound of a Group II metal of the periodic table. Known compounds of Group II metals can be used without any particular restriction. Preferred generally are metal alkoxide compounds represented by the general formula M(OR")$_2$ wherein M is a Group II metal of the periodic table and R" is an alkyl group, and alcohol-soluble organic salts or inorganic salts. Specific examples of the aforesaid compounds generally preferred in this invention include magnesium compounds such as Mg(OCH$_3$)$_2$, Mg(OC$_2$H$_5$)$_2$, Mg(O—iso—C$_3$H$_7$)$_2$, Mg(O—n—C$_4$H$_9$)$_2$, Mg(O—iso—C$_5$H$_{11}$)$_2$, MgCl$_2$, Mg(NO$_3$)$_2$ and Mg(CH$_3$COO)$_2$, and Group II metal compounds corresponding to these magnesium compounds resulting from replacement of Mg by a metal of Group IIa of the periodic table such as Be, Ca, Sr and Ba or a metal of Group IIb of the periodic table such as Zn and Cd. Ca(HOC$_6$H$_4$COO)$_2$.2H$_2$O can also be used preferably.

In the aforesaid process of production, the use of a hydrolysis promoting agent, for example a mineral acid such as hydrochloric acid or nitric acid, or an ion-exchange resin is frequently preferred for promoting the hydrolysis reaction. Accordingly, the hydrolysis promoter may be used as required.

The solvent, the reaction conditions, etc. used in the above process will be described in detail hereinbelow. It is preferred to determine beforehand conditions for calcining the sol- or gel-like product obtained by the aforesaid process in order to obtain a crystalline metal oxide. Generally, the calcination is preferably carried out at a temperature of 950° to 1100° C. for 15 minutes to 2 hours although these conditions may vary depending upon the contents of titanium oxide and the oxide of Group II metal in the crystalline metal oxide. If the contents of titanium oxide and the oxide of Group II metal increase, crystallization tends to occur within a short period of calcination. If the temperature is low or the calcination time is too short, the sol-like or gel-like product may not be crystallized. Moreover, cristobalite or tridymite may form when the calcination temperature is too high. It is recommended therefore to determine these conditions by conducting preliminary tests.

In particular, to produce a spherical (pearl-like) crystalline metal oxide, the following method (1) is a typical preferred embodiment.

(1) A method which comprises adding a mixed solution containing a compound of a Group II metal of the periodic table, a hydrolyzable organic silicon compound and a hydrolyzable titanium compound to an alkaline solvent containing ammonia, an amine compound, etc. and being capable of dissolving the organic silicon compound, the titanium compound and the compound of the Group II metal but substantially incapable of dissolving the reaction product, hydrolyzing said compounds, and calcining the precipitated reaction product gives a spherical crystalline metal oxide.

The solvent in the aforesaid mixed solution may be any solvent which can dissolve the aforesaid starting materials. By reason of reactivity, operability, availability, etc., alcohol solvents such as methanol, ethanol, isopropanol, butanol, isoamyl alcohol, ethylene glycol and propylene glycol are preferred. Ether solvents such as dioxane and diethyl ether and ester solvents such as ethyl acetate may also be used in a minor proportion as a mixture with the alcohol solvents.

Generally, the starting materials are separately dissolved in solvents and then the solutions are mixed. Alternatively, it is possible to add other starting materials to a solution in which one starting material is dissolved, and dissolving the other material to prepare the mixed solution.

A method can also be employed which comprises mixing a solution containing the Group II metal compound and the organic silicon compound in a solvent with a solution containing the titanium compound and the organic silicon compound in a solvent.

Generally, the concentration of the starting materials in the mixed solution is preferably low. If, however, it is too low, the amount of the solvent used increases greatly. If it is too high, the reaction becomes difficult to control, or the solution lends itself to inconvenient handling. Hence, the concentration is determined properly by taking these into consideration. Generally, the suitable concentration of the starting materials in the mixed solution is not more than 50% by weight, preferably 5 to 50% by weight.

To obtain a spherical crystalline metal oxide, it is preferred to control the mole ratio between silicon (Si) and titanium (Ti) in the mixed solution and the amount of water added to the mixed solution. Water in the starting mixed solution comes, for example, from the solvent, or is added positively to hydrolyze the starting organic silicon compound. If the amount of the water is too large, it is generally difficult to obtain spherical particles of a crystalline metal oxide. To obtain the spherical metal oxide, therefore, the amount of water in the mixed solution is preferably small. Generally, good results are obtained by selecting the amount of the water such that the mole ratio of $H_2O/Ti$ is at least 1, preferably at least 2.0, and the mole ratio of $H_2O/Si$ is not more than 4, preferably not more than 1.0.

Depending upon the amounts of the compound of the Group II metal (M) and titanium compound contained in the mixed solution, the crystal form of the calcined product or the calcination temperature and time required for crystallization differ subtly. Preferably, therefore, the amounts of Si, Ti and M are restricted. Generally, it is preferred to select their amounts such that the mole ratio of $(M+Ti)/(Si+M+Ti)$ is from 0.004 to 0.2, preferably from 0.04 to 0.1.

The starting mixed solution prepared as above is then added to an alkaline solvent capable of dissolving the starting materials but substantially incapable of dissolving the reaction product to precipitate an oxide comprising an oxide of the Group II metal, titanium oxide and silicon oxide as main components. The solvent capable of dissolving the starting materials but substantially incapable of dissolving the reaction product is not particularly restricted, and known organic solvents are used. Solvents which are generally used preferably are water-containing solvents composed of alcoholic solvents or mixtures of the alcoholic solvents with a minor proportion of organic solvents such as ether solvents or ester solvents, as exemplified hereinabove as the solvent for the organic silicon compound, the titanium compound and the Group II metal compound, and water. The water-containing solvents should be alkaline as described above. To make the solvents alkaline, known compounds can be used. Generally, ammonia and amine compounds are most preferably used.

The amine compounds may be any known amine compounds, and specific examples include aliphatic amines such as propylamine, dibutylamine, triethylamine and trimethylamine, alicyclic amines such as cyclohexylamine, and aromatic amines such as aniline, dimethylaniline and toluidine.

Since the shape of the crystalline metal oxide obtained in this invention, and especially the particle diameter of the spherical product, are affected by such factors as the type of the organic solvent, the amount of water, the concentration of the alkali, etc., it is preferred to determine these conditions beforehand. Generally, the concentration of the alkali is preferably selected within the range of 1.0 to 10 mol/$10^{-3}$ m$^3$. As the concentration of the alkali is higher, the particle diameter of the resulting metal oxide tends to be larger. The amount of water in the alkaline solvent should be sufficient to promote the hydrolysis and form a metal oxide, and is generally preferably selected within the range of 0.5 to 50 mol/$10^{-3}$ m$^3$. As the concentration of water is higher, the particle diameter of the metal oxide tends to be larger. The particle diameter of the metal oxide is also affected by the type of the organic solvent. Generally, as the number of carbon atoms of the organic solvent becomes larger, the particle diameter of the metal oxide tends to become larger.

The amount of the alkaline solvent is not particularly critical. Generally, the suitable amount of the alkaline solvent is in the range of 100 to 200 parts by volume per 100 parts by volume of the starting mixed solution.

There is no particular limitation on the method of adding the starting mixed solution to the alkaline solvent. Generally, it is preferred to add it little by little over an extended period of time. For example, it may be added at a rate of increase of 0.1 to 1.0 part by volume in a minute per 100 parts by volume of the alkaline solvent.

The reaction temperature varies with various conditions, and cannot be limited in a general manner. Usually, the reaction may be carried out in a temperature range of about 0° to about 40° C., preferably about 10° to about 30° C., under atmospheric pressure. Although the reaction may also be carried out under reduced or elevated pressure, it sufficiently proceeds at atmospheric pressure.

The hydrolysis reaction in the alkaline solvent is generally carried out with stirring. The stirring conditions cannot be generalized because they differ depending upon the mode of stirring, the type and size of stirring vanes, the size and shape of the reactor, the presence or absence of a baffle plate, etc. Usually, the stirring conditions may be selected so that the Reynold's number is within the range of 5,000 to 30,000. In particular, when a spherical product is desired, these conditions are preferably determined by conducting preliminary tests prior to the hydrolysis reaction.

The reaction product obtained by the reaction operation described above is separated and calcined whereby it is crystallized to the crystalline metal oxide of this invention. This fact can be confirmed by X-ray diffraction analysis, differential thermal analysis, etc. For example, the Cu-Kα X-ray diffraction pattern of a sample obtained by calcining the reaction product at 1000° C. for 1 hour and allowing it to cool to room temperature shows a series of peaks having main peaks in the vicinity of $2\theta=26.7°$ and $2\theta=20.9°$, and is similar to the diffraction pattern of known alpha-quartz. Differential thermal analysis shows that the sample has a peak at about 570° C. similar to the transition peak of alpha-quartz⇌beta-quartz.

It has not yet been clear by what mechanism the above crystallization proceeds, but the following presumption is made. By heating the sample, some crystals acting as a nucleus-forming promoter, for example MTiO$_3$ crystals (M is a Group II metal), are formed, whereby a crystal nucleus of beta-quartz occurs in the silicon dioxide phase. The crystal nucleus of beta-quartz grows and the silicon dioxide phase is completely converted to beta-quartz. MTiO$_3$ dissolves in the beta-quartz phase. The product is then allowed to cool to room temperature. As a result, beta-quartz is transformed into alpha-quartz to obtain a metal oxide similar to alpha-quartz, in which MO and TiO$_2$ dissolve to form a solid solution.

The crystalline metal oxide so obtained comprises the oxide of the Group II metal of the periodic table, titanium oxide and silicon oxide as main components, shows a crystal form similar to alpha-quartz in its X-ray diffraction pattern, and has a specific surface area of not more than 100 m$^2$/g. By selecting the various conditions properly as stated hereinabove, there can be obtained a spherical crystalline metal oxide which generally has a particle diameter in the range of 0.1 to 1.0 micron meter and an excellent particle size distribution shown by a standard deviation (defined hereinafter) of the particle diameter of not more than 1.30.

The following method (2) is a typical embodiment of producing a crystalline metal oxide in shapes other than a spherical (pearl-like) shape.

(2) This method comprises dissolving a compound of a Group II metal of the periodic table, a hydrolyzable organic silicon compound and a hydrolyzable organic titanium compound in a solvent capable of dissolving these compounds, hydrolyzing said compounds in said solution or after said solution is added to a separately prepared solvent incapable of dissolving the reaction product, spinning the highly viscous solution before the formation of a sol- or gel-like product and further hydrolyzing the spun product to form a gel-like product, or transferring said solution containing starting materials or the highly viscous solution to a mold and hydrolyzing it within the mold to form a gel-like product, and thereafter calcining the gel-like product.

The method (2) is the same as the method (1) described hereinabove in dissolving the starting compounds in the solvent, but differs from the latter in that the metal oxide is molded into a specific shape until it is converted to a sol or gel and finally a vitreous product. When a metal oxide in the shape of a rod, plate or film is to be obtained finally, the solution of the starting compounds or the solution of a higher viscosity obtained by partial hydrolysis of the starting materials is transferred to a mold, and then hydrolyzed in the mold to form a gel-like product, i.e. a vitreous product, conforming to the shape of the mold. When a film-like metal oxide is finally desired, it is desirable to use a smooth plate as the mold, cast the aforesaid solution onto it, and hydrolyze it with evaporation of the solvent. When it is desired to obtain a fibrous metal oxide, the starting materials are partially hydrolyzed to form a highly viscous solution, and the highly viscous solution is spun into a fibrous form, followed by converting it to a vitreous product.

Preferably, the concentration of the starting materials in the starting solution is generally high. Advantageously, the concentration of the starting materials in said solution is generally at least 50% by weight, preferably 50 to 95% by weight.

Addition of water, an acid or an alkali is a preferred means of promoting hydrolysis in the above reaction. In particular, hydrochloric acid and aqueous ammonia are frequently used conveniently. When it is desired to obtain a fibrous or film-like crystalline metal oxide, the use of hydrochloric acid is preferred. If the amount of water, the acid or alkali is too large, the resulting metal oxide tends to be irregularly shaped. Accordingly, when it is desired to obtain the crystalline metal oxide in a specific shape such as a fiber or film, the amount of water, the acid or alkali in the mixed solution is preferably small. Generally, good results are obtained if it is selected such that the mole ratio of H$_2$O/Si is not more than 5.0, preferably not more than 2.0, the mole ratio of (H$^+$)/Si is not more than 0.3, preferably not more than 0.03, and the mole ratio of (OH$^-$)/Si is not more than 0.3, preferably not more than 0.03.

The time required to obtain the gel-like product by hydrolysis varies depending upon the amount of water, the acid or the alkali added, the method of storing the mixed solution, or the temperature of the mixed solution. Generally, when the mixed solution is stored at a temperature of 20° to 30° C. in a container closed with an air-permeable cover, the gel-like product is obtained in 1 to 60 days.

To obtain a fibrous crystalline metal oxide, the solution having an increased viscosity, for example a solution having a viscosity of 10 to 1000 poises, preferably 50 to 500 poises, is spun into fibers. In the case of a film, the highly viscous solution is cast on a smooth flat surface and formed into a film by a customary method. The time required for the mixed solution to become viscous varies depending upon the aforesaid conditions, but generally 1 hour to 7 days is satisfactory.

The resulting fibrous, film-like, plate-like, rod-like or irregularly shaped oxide is calcined generally at a temperature of 950° to 1100° C. to form a crystalline metal oxide whose X-ray diffraction pattern is similar to that of alpha-quartz.

Since the crystalline metal oxide of this invention has a crystal form similar to alpha-quartz, it can be used directly in fields where alpha-quartz has previously been used. Furthermore, since the crystalline metal oxide of this invention can assume various shapes, it is widely applicable according to these shapes. For example, a spherical product is an excellent inorganic filler. Plate-like and rod-like products are suitable for use in tableware, component parts of electronic cooking ranges and heat resistant windowpanes. A fibrous product can be suitably used as various filters. A film-like product is widely used as an anticorrosive protective film.

The method of using the crystalline metal oxide of this invention in a typical application is shown below.

Because of its excellent properties, the crystalline metal oxide of the invention can be an excellent filler of a composite resin used for example as a restorative material.

A description of the metal oxide of the invention follows with respect to its use as a powdery component of a composite resin used for dental restorative material.

A composite material composed, for example, of a polymerizable vinyl monomer and the spherical crystalline metal oxide of the invention having a particle diameter of, for example, 0.1 to 1.0 micrometer exhibits excellent properties.

One component of the composite material is a polymerizable vinyl monomer. There is no particular limitation on the vinyl monomer, and any known vinyl monomers generally used in dental composites can be used. Typically, the vinyl monomer is a vinyl monomer having an acryloyl and/or a methacryloyl group. Specific examples of the vinyl monomer having an acryloyl group and/or a methacryloyl group include 2,2-bis[4-(2-hydroxy-3-methacryloxypropoxy)phenyl]propane, methyl methacrylate, bismethacryloethoxyphenylpropane, triethyleneglycol dimethacrylate, diethylene glycol dimethacrylate, tetramethylol triacrylate, tetramethylolmethane trimethacrylate, tetramethylolmethane tetraacrylate and trimethylolethane trimethacrylate. Vinyl monomers having a urethane structure represented by the following structural formula can also be conveniently used.

In the formula, $R_1$, $R_2$, $R_3$ and $R_4$ each represent H or $CH_3$, and $-\!\!+\!\!A\!\!+\!\!-$ is preferably These vinyl monomers are known as dental materials, and can be used either singly or in combination as required.

The other component of the composite material is the crystalline metal oxide. Preferably, spherical particles of the crystalline metal oxide having a particle diameter of 0.1 to 1.0 micrometer and a standard deviation (defined hereinafter) of the particle size distribution of not more than 1.30 are used. The particle diameter, the shape and the particle size distribution of the metal oxide are very important factors as far as it is used in a composite resin for dental use. For example, if the particle diameter of the metal oxide is less than 0.1 micrometer, there is a marked rise in viscosity when it is kneaded with the polymerizable monomer to form a paste-like mixture. An attempt to prevent the viscosity rise by increasing the proportion of the metal oxide to be blended results in reduced operability. Hence, a substantially practical material cannot be obtained. If the particle diameter is larger than 1.0 micrometer, the abrasion resistance or the surface smoothness of the resin after polymerization of the vinyl monomer is reduced, and its surface hardness is also decreased. If the standard deviation (defined hereinafter) of the distribution of the particle size is larger than 1.30, the operability of the composite material is reduced to an extent that it cannot be used in practical applications. Particles of the crystalline metal oxide which have a particle diameter in the range of 0.1 to 1.0 micrometer and a standard deviation (defined hereinafter) of the particle size distribution which is not more than 1.30 but which are not spherical do not prove to be satisfactory in abrasion resistance, surface smoothness, surface hardness, etc. When the above composite material is used as a composite resin for dental restorative material, its operability becomes an important factor, and the mechanical strength, abrasion resistance, surface smoothness, etc. of the resulting cured composite resin should be maintained at sufficiently good levels. For this purpose, the amount of the crystalline metal oxide in a composite resin is generally selected from the range of 60 to 90% by weight.

For use as a composite resin for dental restorative material, it is generally preferred to employ a method wherein a paste-like mixture composed of the crystalline metal oxide, the polymerizable vinyl monomer and a polymerization promoter (e.g., a tertiary amine compound), and a paste-like mixture composed of the vinyl monomer and a polymerization initiator (for example, an organic peroxide such as benzoyl peroxide) are separately prepared in advance, and immediately before the restorative material operation, the two paste-like mixtures are kneaded, filled in a prepared tooth and then cured. The composite resin obtained by curing the aforesaid composite material has comparable mechanical strength such as compression strength to conventional composite resins and better abrasion resistance and surface smoothness, higher surface hardness and better transparency than the latter and it can be very easily finished by surface polishing. No clear reason has yet been elucidated for these excellent advantages, but the present inventors have the following theoretical speculation. Firstly, by using crystalline metal oxide particles having a spherical shape and a uniform particle diameter shown by a standard deviation (defined hereinafter) of the particle size distribution of not more than 1.30, the crystalline metal oxide is more uniformly and densely packed in the resulting cured composite resin than in the case of using a conventional filler having a broad particle size distribution and a non-uniform particle shape. Secondly, by using crystalline metal oxide particles having a particle diameter in the range of 0.1 to 1.0 micrometer, the polished surface of the cured composite resin is more smooth than in the case of using a conventional inorganic filler having a particle diameter on the order of several tens of micrometers. Furthermore, the total specific surface area of the metal oxide filler is smaller than in the case of using an ultrafine filler containing fine particles having a particle diameter on the order of several tens of nanometers as a main component. Hence, under conditions permitting proper operability, the amount of the filler can be increased.

In addition to the aforesaid characteristic features ascribable to the shape of the crystalline metal oxide of this invention, it is easy to cause the refractive index of the metal oxide filler in accordance with this invention to correspond with that of a polymer of the vinyl monomer, and by so doing, a composite resin having excellent transparency can be obtained.

The aforesaid composite material exhibit various unexpected advantages by blending the specific crystalline metal oxide and the polymerizable vinyl monomer. In addition to the two components, other additives generally used in dental restorative materials may be added to the composite material as required. Typical examples of the these additives are radical polymerization inhibitors, coloring pigments for color matching, and ultraviolet absorbers.

The following examples illustrate the present invention more specifically. Unless otherwise specified, the various properties referred to in these examples were measured by the following methods.

(1) Refractive index

A solvent system having the same refractive index as a sample crystalline metal oxide was prepared, and the refractive index of the solvent was taken as the refractive index of the sample. Specifically, the solvent system was prepared by suspending the sample in solvents and the composition of the solvent system which permitted the suspension to look transparent by visual observation was determined at a constant temperature (20° C.). n-Pentane, n-hexane, cyclohexane, toluene, styrene and methylene iodide were used as the solvents, and the refractive index of the solvent system having the aforesaid composition was measured by the Abbe's refractometer.

(2) Specific viscosity

The specific viscosity was measured by the pycnometer method.

(3) Particle diameter and the standard deviation of the particle size distribution.

A powdery sample of the metal oxide was photographed under a scanning electron microscope. The number (n) of particles observed within a unit visual field of the photograph and the particle diameter (diameter Xi) were determined. The standard deviation was calculated in accordance with the following equation:

$$\text{Standard deviation} = \frac{\overline{X} + \sigma_{n-1}}{\overline{X}}$$

wherein $\overline{X} = \dfrac{\sum\limits_{i=1}^{n} Xi}{n}$ (number average particle size)

$$\sigma_{n-1} = \sqrt{\frac{\sum\limits_{i=1}^{n} (Xi - \overline{X})^2}{n-1}}$$

(4) Specific surface area

Measured according to the BET method by means of a rapid surface area measuring device SA-1000 made by Shibata Kagaku Kiki Kogyo K.K.

(5) Preparation and curing of a paste of a composite material

The crystalline metal oxide surface-treated with gamma-methacryloxypropyltrimethoxysilane and a vinyl monomer in predetermined proportions were put in an agate mortar and fully kneaded until a uniform paste was formed. The paste was then divided into two equal portions. One portion was fully mixed with a polymerization promoter (to form a paste A). The other paste portion was fully mixed with an organic peroxide catalyst (to form a paste B). Equal amounts of the paste A and the paste B were kneaded for 30 seconds. The mixture was filled in a mold and cured.

(6) Compression strength

The paste A and the paste B were kneaded, and polymerized at room temperature for 30 minutes. The product was immersed in water at 37° C. for 24 hours to form a test specimen. The test specimen was cylindrical with a diameter of 6 mm and a height of 12 mm. The test specimen was mounted on a tester (UTM-5T made by Toyo-Baldwin Company), and its compression strength was measured at a corsshead speed of 10 mm/min.

(7) Flexural strength

The paste A and the paste B were kneaded and polymerized at room temperature for 30 minutes. The product was immersed in water at 37° C. for 24 hours to form a test specimen. The test specimen was in the shape of a square pillar having a size of 2×2×25 mm. A bending tester having an interfulcrum distance of 20 mm was mounted on UTM-5T (made by Toyo-Baldwin Company), and the test specimen was subjected to a bending test at a crosshead speed of 0.5 mm/min.

(8) Toothbrush abrasion depth and surface roughness

The paste A and the paste B were mixed and polymerized at room temperature for 30 minutes. The product was immersed in water at 37° C. for 24 hours to form a test specimen. The test specimen was in the form of a plate having a size of 1.5×10×10 mm. The test specimen was rubbed along a length of 1500 meters by a toothbrush under a load of 400 g, and then the 10-point height of irregularities was calculated by a surface roughness tester (SURFCOM A-100).

The abrasion depth was calculated by dividing the abraded weight by the density of the composite resin.

(9) Surface hardness

The paste A and the paste B were kneaded, and polymerized at room temperature for 30 minutes. The product was immersed in water at 30° C. for 24 hours to form a test specimen. The test specimen was in the shape of a disc having a size of 2.5×10 mm. The surface hardness of the specimen was measured by using a micro-Brinell hardness tester.

The abbreviations used in these examples were as follows unless otherwise indicated.

IPA: isopropanol
MeOH: methanol
BuOH: butanol

EXAMPLE 1

Water (0.9 g) and 104 g of distilled tetraethyl silicate [Si(OC$_2$H$_5$)$_4$; Ethyl Silicate 28, a tradename for a product of Nippon Calcoat Chemical Co., Ltd.] were dissolved in 0.5 liter of methanol. The tetraethyl silicate was partly hydrolyzed in the solution at room temperature for about 2 hours with stirring. The solution was added with stirring to a solution of 8.5 g of titanium tetrabutoxide (Ti(O—nC$_4$H$_9$)$_4$ made by Nippon Soda Co., Ltd.) in 0.5 liter of isopropanol to prepare a mixed solution (A) of the partial hydrolyzate of tetraethyl silicate and titanium tetrabutoxide. Then, 3.8 g of strontium bismethoxide and 104 g of tetraethyl silicate were dissolved in 1.0 liter of methanol. The solution was refluxed for 30 minutes at 75° C. in an atmosphere of nitrogen. The temperature was then returned to room temperature to prepare a mixed solution (B). The mixed solution (A) and the mixed solution (B) were mixed at room temperature to form a mixed solution (C).

Methanol (2.5 liters) was placed in a 10-liter glass reactor equipped with a stirrer, and 500 g of an aqueous solution of ammonia (concentration 25% by weight) was added to methanol to form a methanol solution containing ammonia. The solution was maintained at 20° C., and with stirring, the mixed solution (C) prepared previously was added over the course of about 4 hours. In several minutes after the start of addition, the reaction solution became milk-white. After the addition, the stirring was continued further for 1 hour, and the solvent was removed from the milk-white reaction solution by an evaporator to obtain a milk-white powder. The powder was then calcined at 1000° C. for 45 minutes to form a metal oxide.

A scanning electron microphotograph of the metal oxide showed that the powdery metal oxide was spherical and had a particle diameter in the range of 0.12 to 0.26 micrometer. The standard deviation of its particle size distribution was 1.06.

The resulting metal oxide had a specific surface area of 17 m$^2$/g, a specific gravity of 2.65 and a refractive index of 1.55 to 1.56.

The Cu-K$\alpha$ X-ray diffraction pattern of the milk-white powder before calcination was a broad curve free from specific peaks which is inherent to an amorphous material. On the other hand, the Cu-K$\alpha$ X-ray diffraction pattern (2$\theta$) of the metal oxide obtained after calcination showed characteristic peaks at 26.7° and 20.9°, and also had peaks at 36.6°, 39.5°, 40.4°, 42.5°, 45.8°, 50.2°, 54.9° and 60.0°, as shown in FIG. 1.

Figure 1:
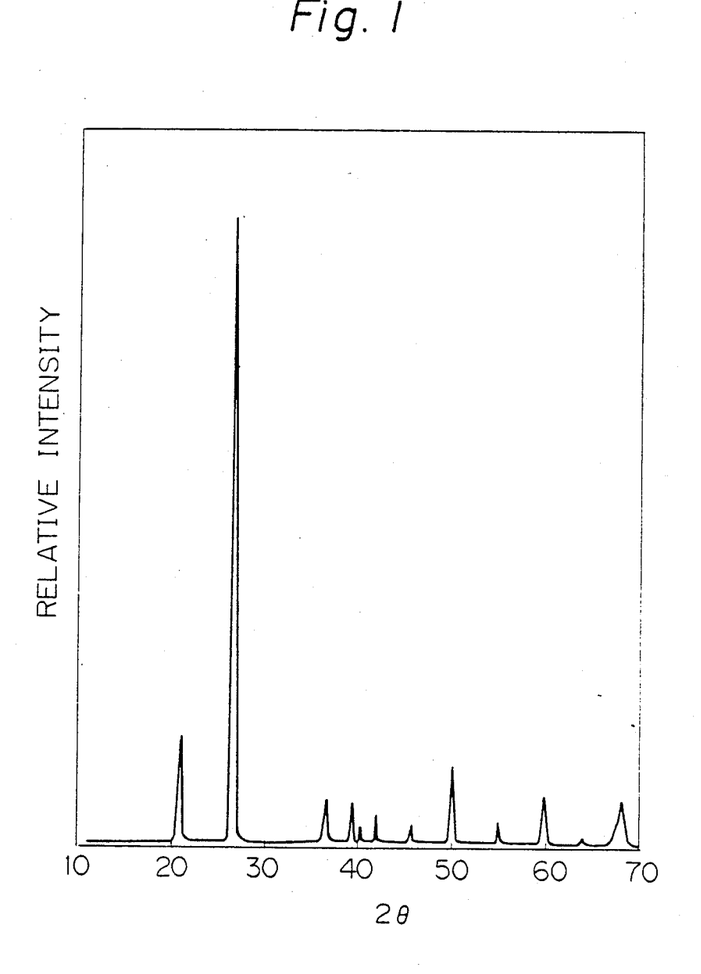
FIG. 1 is an X-ray diffraction pattern of the metal oxide solid solution obtained in Example 1 of the invention.
Figure 2:
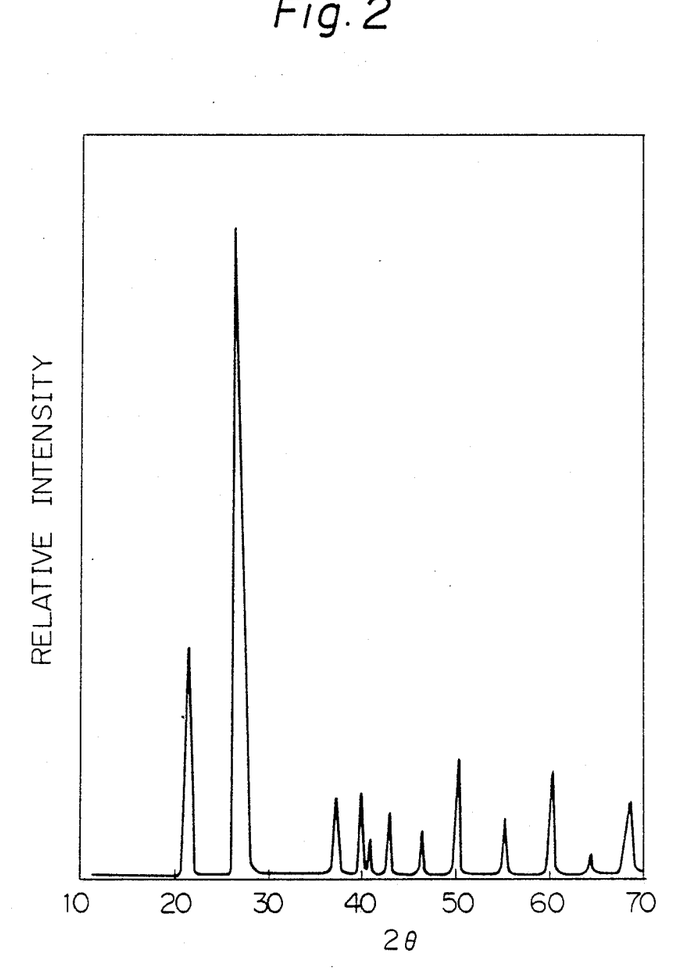
FIG. 2 is an X-ray diffraction pattern of an authentic sample of alpha-quartz.

FIG. 2 shows the Cu-K$\alpha$ X-ray diffraction pattern of alpha-quartz. A comparison of FIG. 1 with FIG. 2 shows that the X-ray diffraction patterns are very similar to each other, and the metal oxide obtained above is a crystalline metal compound having a crystal form similar to alpha-quartz.

The X-ray diffraction pattern in FIG. 1 shows that the metal oxide did not have peaks showing crystals of TiO$_2$, SrO or SrTiO$_3$.

Differential thermal analysis showed that the metal oxide had an endothermic peak in the vicinity of 570° C.

The contents of TiO$_2$ and SrO in the crystalline metal oxide determined by fluorescent X-ray analysis corresponded nearly with the values calculated from the amounts of the starting materials charged. The content of TiO$_2$ in the powder was found to be 2.4 mole % (calculated 2.4 mole %); the content of SrO$_2$ was found to be 2.4 mole % (calculated 2.4 mole %); and the amount of the powder yielded was found to be 63.0 g (calculated 64.7 g).

EXAMPLES 2 TO 4

In each run, Example 1 was repeated except that the organic silicon compound, the Group II metal compound, the titanium compound and water shown in Table 1 were used. The results are also shown in Table 1. The crystalline metal oxides obtained in these examples were found to be spherical by observation of their scanning electron microphotographs.

EXAMPLES 5 TO 7

In each run, Example 1 was repeated except that a mixed solution (A) having the composition shown in Table 2 was used. The results are also shown in Table 2. The crystalline metal oxides obtained in these examples were found to be spherical by observation of their scanning electron microphotographs.

EXAMPLES 8 TO 10

In each run, Example 1 was repeated except that the alcoholic solution containing ammonia as shown in Table 3 was used. The results are shown in Table 3. The resulting crystalline metal oxides were found to be spherical by observation of their scanning electron microphotographs.

EXAMPLES 11 TO 14

In each run, Example 1 was repeated except that the conditions shown in Table 4 were used. The resulting crystalline metal oxides obtained were found to be spherical by observation of their scanning electron microphotographs.

Figure 3:
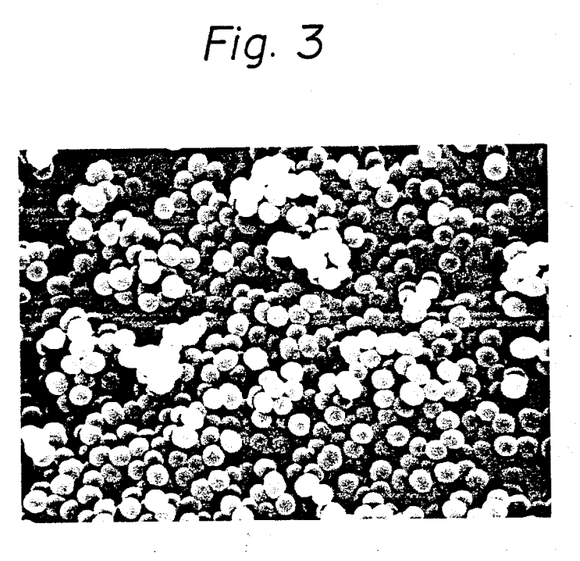
FIG. 3 is a scanning electron microphotograph of the metal oxide obtained in Example 12.

A scanning electron microphotograph (magnification 15,000) of the crystalline metal oxide solid solution composed of $SiO_2$, $TiO_2$ and CaO obtained in Example 12 is shown in FIG. 3 of the accompanying drawings.

EXAMPLE 15

Example 12 was repeated except that the amount of calcium bismethoxide was changed to 5.4 g; the amount of titanium tetrabutoxide added, to 16.8 g; the amount of tetraethyl silicate added, to 208 g; and the calcination time, to 12 minutes. The resulting metal oxide was a solid solution containing 4.5 mole % of each of CaO and $TiO_2$. It was pearl-like and had a specific surface area of 16 $m^2/g$, a refractive index of 1.55 to 1.56, and a particle diameter of 0.15 to 0.25 micrometer. The Cu-K$\alpha$ X-ray diffraction pattern of the metal oxide was similar to that shown in FIG. 1, and it was seen that the resulting metal oxide had a crystal form similar to alpha-quartz. The interplanar spacings (d, Å) calculated by the Bragg's equation from the X-ray diffraction pattern are shown in Table 5. Table 5 also shows the interplanar spacings calculated from the X-ray diffraction pattern of natural alpha-quartz and the interplanar spacings calculated from the X-ray diffraction pattern of a metal oxide solid solution containing 2.4 mole % each of CaO and $TiO_2$.

EXAMPLE 16

0.075 g of 0.1% hydrochloric acid, 20.8 g of tetraethyl silicate and 0.25 g of anhydrous calcium chloride were dissolved in 10 ml of methanol. The solution was stirred at room temperature for about 1 hour. The solution was then added to a solution of 0.71 g of titanium tetrabutoxide in 10 ml of isopropanol to form a mixed solution.

The mixed solution was then transferred to a 100 ml vinyl chloride resin beaker. The open part of the beaker was covered with a plastic film and about 20 pinholes were provided by a needle (outside diameter about 1 mm). The beaker was stored in a constant temperature chamber 25° C. In 2 weeks, a transparent vitreous plate was formed at the bottom of the beaker. Thereafter, the number of pinholes in the film was increased to about 50, and the beaker was further stored for 1 month in the constant temperature chamber. Thereafter, the plastic cover was removed, and the beaker was further stored in the constant temperature chamber for 2 months. In this condition, almost all of the solvent evaporated, and a vitreous plate was left at the bottom of the beaker. The plate was heated to 45° C. at a temperature elevating rate of 0.1° C./min. and maintained at 45° C. for 3 days. Then, it was further heated to 100° C. at a temperature elevating rate of 0.1° C./min. and maintained at 100° C. for 1 day. The plate so obtained scarcely contained the alcohol and water used. The plate was heated at a temperature elevating rate of 0.1° C./min., and calcined at 1000° C. for 1 hour.

The Cu-K$\alpha$ X-ray diffraction pattern (2$\theta$) of the calcined plate showed a series of peaks including main peaks at 26.7° and 20.9° which were nearly the same as FIG. 1. This suggested the similarity of the crystal form of the plate-like oxide to that of alpha-quartz. The plate-like oxide had a specific gravity of 2.64 and a refractive index of 1.55 to 1.56. The contents of $TiO_2$ and CaO of the crystalline metal oxide determined by fluorescent X-ray analysis corresponded with the values calculated from the amounts of the starting compounds charged, and the weight of the resulting plate-like product also corresponded with the value calculated from the amounts of the charged materials. The $TiO_2$ content of the crystalline oxide was found to be 2.0 mole % (calculated 2.0 mole %). The CaO content of the crystalline oxide was found to be 2.0 mole % (calculated 2.0 mole %). The weight of the plate-like crystalline metal oxide was found to be 6.3 g (calculated from the charged amounts 6.3 g).

EXAMPLE 17

Water (1.8 g), 0.075 g of 0.1% hydrochloric acid, 20.8 g of tetraethyl silicate and 0.23 g of anhydrous calcium chloride were dissolved in 10 ml of methanol. The solution was stirred at room temperature for about 1 hour. The solution was then added to a solution of 0.71 g of titanium tetrabutoxide in 10 ml of isopropanol to form a mixed solution. The mixed solution was stored for 5 days in a constant temperature chamber at 25° C., and consequently became viscous (about 150 poises) and spinnable. A fibrous gel-like product was obtained by dipping the tip of a glass rod in the viscous solution and then pulling it up in the air to form the viscous solution into a filament. The gel-like product was calcined under the same calcination conditions as in Example 16 to obtain a fibrous crystalline metal oxide.

An electron microphotograph of the product showed that the fibrous oxide had a diameter of 10 to 100 microns and an average length of about 20 cm. The refractive index, specific gravity, X-ray diffraction pattern and $TiO_2$ and CaO contents of the products measured were the same as in Example 16.

EXAMPLE 18

The same mixed solution as prepared by the method of Example 16 was transferred to an enamelled tray (25 cm × 18 cm × 3 cm) and the open part of the tray was covered with an aluminum foil. About 50 pinholes were provided in the aluminum foil by a needle (outside diameter about 1 mm). The tray was stored for one week in a constant temperature chamber at 25° C. while being maintained horizontal. During this time, the hydrolysis and polymerization proceeded and the solvent was volatilized. A vitreous film having a thickness of about 100 microns was formed at the bottom of the tray. When the aluminum cover was removed, cracks occurred in the film, and it could be easily taken out of the tray. The film-like metal oxide was calcined under the same calcination conditions as in Example 16 to obtain a film-like crystalline metal oxide solid solution.

The refractive index, specific viscosity, X-ray diffraction pattern and $TiO_2$ and CaO contents of the resulting film-like crystalline metal oxide measured were the same as those in Example 16.

EXAMPLE 19

A mixed solution prepared by the same method as in Example 16 was transferred to a cylindrical vinyl chloride resin container (inside diameter 1.5 cm, length 10 cm) having one end portion sealed. The container was set upright with its open portion up. The open portion was not covered, and the mixed solution held in the container was stored for about 3 months in a constant temperature chamber at 25° C. During this period, the starting mixed solution was hydrolyzed and gelled to form a cylindrical oxide. The oxide was calcined under the same calcination conditions as in Example 16 to form a rod-like metal oxide having an outside diameter of 1.1 cm and a length of 3.5 cm. X-ray diffraction analysis showed that the resulting rod-like metal oxide had a crystal form similar to alpha-quartz.

The refractive index, specific gravity, X-ray diffraction pattern and $TiO_2$ and CaO contents of the crystalline metal oxide measured were the same as in Example 16.

EXAMPLE 20

A crystalline metal oxide synthesized by the same method as in Example 1 was surface-treated with gamma-methacryloxypropyltrimethoxysilane by adding 6% by weight of gamma-methacryloxypropyl trimethoxysilane to the crystalline metal oxide, refluxing the mixture at 80° C. for 2 hours in a water-ethanol solvent, removing the solvent by an evaporator, and then drying the product in vacuum.

The crystalline metal oxide was fully kneaded with a mixture of bisphenol A diglycidyl methacrylate (to be referred to as Bis-GMA) and triethylene glycol dimethacrylate (to be referred to as TEGDMA) as vinyl monomers (the mixing ratio of Bis-GMA/TEGDMA=2/7 mole ratio) to form a paste-like composite material. The amount of the crystalline metal oxide filled in the composite material was 73.6% by weight, and the viscosity of the paste was proper for operation. The paste was then divided into two equal portions. N,N-dimethyl-p-toludine as a polymerization promoter was added to one portion, and benzoyl peroxide as a polymerization initiator, to the other, each in an amount of 1% by weight based on the vinyl monomer, to form a paste A and a paste B, respectively.

Equal amounts of the paste A and the paste B were kneaded for 30 seconds and cured at room temperature. The cured product was found to have a compression strength of 3.750 $kg/cm^2$, a flexural strength of 850 $kg/cm^2$, a surface roughness of 0.6 micrometer, a surface hardness of 65.0 and a toothbrush abrasion depth of 5.4 micrometers. The surface of the product was finished by polishing with Sof-lex (3M Company). A surface having good smoothness could be easily obtained without excessive shaving of the surface of the composite resin. The product also had good translucency.

EXAMPLES 21 TO 23

Using the crystalline metal oxides of Examples 2, 11 and 12 and the same vinyl monomers as in Example 20, pastes were prepared and cured by the same methods. The properties of the resulting composite resins were measured, and the results are summarized in Table 6.

EXAMPLES 24 TO 26

Paste-like composite materials were prepared in the same way as in Example 20 except that the crystalline metal oxide used in Example 20 was used, and U-4HMA, U-4TMA, U-4BMA, tetramethylolmethane triacrylate (to be referred to as TMMT) and methyl methacrylate (to be referred to as MMA) were used as vinyl monomers. The mixing propertions of the vinyl monomers are shown in Table 7.

The paste-like composite materials were each cured by the same operation as in Example 20, and the properties of the composite resins were measured. The results are also shown in Table 7.

TABLE 1

| | Amounts of the Starting Materials in the Mixed Solution* | | | | | Properties of the Crystalline Metal Oxide | | | | | |
|---|---|---|---|---|---|---|---|---|---|---|---|
| | Mixed Solution (A) | | | Mixed Solution (B) | | Specific Surface | Main peaks in the X-ray | Re- | | Particle diameter | |
| Example | $Si(OC_2H_5)_4$ (g) | Water (g) | $Ti(OC_4H_9)_4$ (g) | $Si(OC_2H_5)_4$ (g) | $Sr(OCH_3)_2$ (g) | Area ($m^2/g$) | diffraction pattern (2θ) | fractive index | Specific gravity | range (μm) | Standard deviation |
| 2 | 104 | 0.8 | 7.1 | 104 | 3.1 | 18 | 26.7° 20.9° | 1.55–1.56 | 2.65 | 0.12–0.24 | 1.08 |
| 3 | 104 | 1.2 | 10.9 | 104 | 4.8 | 15 | 26.7° 20.9° | 1.55–1.56 | 2.66 | 0.10–0.23 | 1.09 |
| 4 | 104 | 1.8 | 16.8 | 104 | 7.4 | 12 | 26.5° 20.7° | 1.54–1.55 | 2.67 | 0.12–0.25 | 1.10 |

*In the mixed solution (A), a mixed solvent composed of 0.2 liter of methanol and 1.0 liter of isopropanol was used. In the mixed solution (B), 1.0 liter of methanol was used as a solvent.

TABLE 2

| | Composition of the Mixed Solution (A) | | | | Properties of the Crystalline Metal Oxide | | | | |
|---|---|---|---|---|---|---|---|---|---|
| Example | Organic silicon compound (g) | Water (g) | $Ti(OC_4H_9)_4$ (g) | Alcohol (l) | Specific Surface area ($m^2/g$) | Main peaks in the X-ray diffraction pattern ($2\theta$) | Refractive index | Particle diameter range ($\mu m$) | Standard deviation |
| 5 | $Si(O-isoC_3H_7)_4$ 132 | 0.9 | 8.5 | IPA = 0.5 MeOH = 0.2 | 15 | 26.7° 20.9° | 1.55–1.56 | 0.15–0.24 | 1.09 |
| 6 | $Si(O-nC_4H_9)_4$ 160 | 0.9 | 8.5 | IPA = 0.5 MeOH = 0.2 | 16 | 26.7° 20.9° | 1.55–1.56 | 0.17–0.26 | 1.12 |
| 7 | Ethyl Silicate 40 75 | 0.9 | 8.5 | IPA = 0.5 MeOH = 0.2 | 18 | 26.7° 20.9° | 1.55–1.56 | 0.12–0.22 | 1.18 |

TABLE 3

| | Composition of the Ammoniac Alcohol | | | | Properties of the Crystalline Metal Oxide | | | | |
|---|---|---|---|---|---|---|---|---|---|
| Example | Ammonia (g) | Water (g) | Alcohol (g) | Temperature (°C.) | Specific surface area ($m^2/g$) | Main peaks in the X-ray diffraction pattern ($2\theta$) | Refractive index | Particle diameter range ($\mu m$) | Standard deviation |
| 8 | 125 | 375 | MeOH = 1.25 IPA = 1.25 | 20 | 15 | 26.7° 20.9° | 1.55–1.56 | 0.20–0.30 | 1.08 |
| 9 | 125 | 375 | IPA = 2.5 | 20 | 11 | 26.7° 20.9° | 1.54–1.55 | 0.30–0.45 | 1.13 |
| 10 | 125 | 375 | BuOH = 2.5 | 20 | 9 | 26.7° 20.9° | 1.54–1.55 | 0.30–0.55 | 1.20 |

TABLE 4

Composition of the Mixed Solution (*1)

| | Mixed solution (A) | | | Mixed Solution (B) | |
|---|---|---|---|---|---|
| Example | $Si(OC_2H_5)_4$ | Water | $Ti(OC_4H_9)_4$ | $Si(OC_2H_5)_4$ | Organic compound of Group II metal |
| 11 | 104 | 1.8 | 12.8 | 104 | $Mg(OCH_3)_2$ 4.3 |
| 12 | 104 | 1.8 | 8.5 | 104 | $Ca(OCH_3)_2$ 2.6 |
| 13 | 104 | 1.8 | 12.8 | 104 | $Ba(O-iso-C_5H_{11})_2$ 11.7 |
| 14 | 104 | 1.8 | 8.5 | 104 | $CaCl_2$ 2.8 |

| Example | Calcination time (hours) | Specific surface area ($m^2/g$) | Main peaks in the X-ray diffraction pattern ($2\theta$) | Refractive index | Specific gravity | Particle diameter range ($\mu m$) | Standard deviation |
|---|---|---|---|---|---|---|---|
| 11 | 2.0 | 14 | 26.7° (*2) 20.9° | 1.54–1.55 | 2.65 | 0.15–0.25 | 1.05 |
| 12 | 1.0 | 17 | 26.7° 20.9° | 1.55–1.56 | 2.66 | 0.12–0.22 | 1.06 |
| 13 | 2.5 | 13 | 26.7° (*2) 20.9° | 1.54–1.55 | 2.67 | 0.17–0.27 | 1.18 |
| 14 | 1.0 | 14 | 26.7° 20.9° | 1.55–1.56 | 2.66 | 0.13–0.23 | 1.20 |

(*1): In the mixed solution (A), a mixed solvent composed of 0.2 liter of methanol and 1.0 liter of isopropanol was used. In the mixed solution (B), 1.0 liter of methanol was used.
(*2): Containing less than about 10% of amorphous silicon dioxide.

TABLE 5

| Interplanar spacing | Miller Index | | | | | | | | | |
|---|---|---|---|---|---|---|---|---|---|---|
| | (100) | (101) | (110) | (102) | (111) | (200) | (201) | (112) | (202) | (211) |
| Natural alpha-quartz | 4.26 | 3.343 | 2.458 | 2.282 | 2.237 | 2.128 | 1.980 | 1.817 | 1.672 | 1.541 |
| Solid solution containing 2.4 mole % of each of CaO and $TiO_2$ | 4.250 | 3.339 | 2.455 | 2.281 | 2.227 | 2.127 | 1.980 | 1.817 | 1.670 | 1.542 |
| Solid solution containing 4.5 mole % of each of CaO and $TiO_2$ | 4.270 | 3.351 | 2.468 | 2.287 | 2.243 | 2.132 | 1.985 | 1.824 | 1.675 | 1.547 |

TABLE 6

| Example | Filler | Amount of the filler in a composite material (wt %) | Properties of the Cured Composite Resin | | | | | |
|---|---|---|---|---|---|---|---|---|
| | | | Compression strength (kg/cm²) | Flexural strength (kg/cm²) | Toothbrush abrasion depth (μm) | Surface roughness (μm) | Surface hardness (H_B) | Transparency |
| 21 | metal oxide of Example 2 | 73.1 | 3400 | 940 | 4.8 | 4.6 | 62 | good |
| 22 | metal oxide of Example 11 | 72.7 | 2200 | 1050 | 4.4 | 0.4 | 63 | good |
| 23 | metal oxide of Example 12 | 72.9 | 3300 | 900 | 5.3 | 0.4 | 62 | good |

TABLE 7

| Example | Vinyl* monomers | Amount of the filler in a composite material (wt %) | Properties of the Cured Composite Resin | | | | | |
|---|---|---|---|---|---|---|---|---|
| | | | Compression strength (kg/cm²) | Flexural strength (kg/cm²) | Toothbrush abrasion depth (μm) | Surface roughness (μm) | Surface hardness (H_B) | Transparency |
| 24 | U-4HMA (45) TMMT (45) MMA (10) | 73.1 | 4100 | 840 | 4.3 | 0.5 | 62 | good |
| 25 | U-4TMA (45) TMMT (45) MMA (10) | 73.0 | 4300 | 900 | 2.9 | 0.6 | 62 | good |
| 26 | U-4BMA (45) TMMT (45) MMA (10) | 73.3 | 4300 | 850 | 3.6 | 0.5 | 63 | good |

*The parenthesized figures attached to the vinyl monomers represent mixing proportions in % by weight.

What is claimed is:

1. Spherical particles comprising a crystalline metal oxide in the form of a solid solution comprising (i) 0.2 to 5 mole% of an oxide of a Group II metal of the periodic table, (ii) 0.2 to 5 mole% of titanium oxide and (iii) at least 91 mole% of silicon oxide as main components and having main peaks at about 26.7° and about 20.9° in its Cu-Kα X-ray diffraction pattern (2θ), a specific refractive index of 1.53 to 1.60 and a particle diameter of 0.1 to 1.0 micrometer.

2. The spherical particles of claim 1 wherein the Group II metal is calcium, magnesium, barium or strontium.

3. The spherical particles of claim 1 wherein the refractive index is 1.53 to 1.57.

4. A process for producing spherical particles comprising a crystalline metal oxide in the form of a solid solution comprising (i) an oxide of a metal of Group II of the periodic table, (ii) titanium oxide and silicon oxide as main components and having main peaks at about 26.7° and about 20.9° in its Cu-Kα X-ray diffraction pattern (2θ), a refractive index of 1.53 to B 1.60 and a particle diameter of 0.1 to 1.0 micrometer, which comprises partially hydrolyzing a hydrolyzable organic silicon compound in an organic solvent, mixing the partially hydrolyzed product, a hydrolyzable compound of a metal of Group II of the periodic table and a hydrolyzable organic titanium compound in an organic solvent, adding the mixed solution to a hydrous alcoholic solution containing ammonia or an amine compound to form a reaction product, and thereafter calcining the reaction product at a temperature and for a period of time sufficient to crystallize said product, the amounts of the Group II metal compound, the titanium compound and the silicon compound being such that the crystalline metal oxide is comprised of from about 0.2 to 5 mole percent of the Group II metal oxide, from about 0.2 to 5 mole percent of the titanium oxide and not less than about 91 mole percent of silicon oxide.

5. The process of claim 4 wherein the mixed solution contains Si, Ti and the metal (M) of the Group II metal compound in such amounts that the mole ratio of (Ti+M)/(Si+Ti+M) is from 0.004 to 0.1.

6. The process of claim 4 wherein the mixed solution contains Si, Ti and the metal (M) of the Group II metal compound in such proportions that the mole ratio of (Ti+M)/(Si+Ti+M) is from 0.02 to 0.1.

7. The process of claim 4 wherein the calcination temperature is 950° to 1100° C.

8. A composite material comprising (a) a polymerizable vinyl monomer and (b) spherical particles comprising a crystalline metal oxide in the form of a solid solution comprising (i) from about 0.2 to 5 mole% of an oxide of a metal of Group II of the periodic table, (ii) from about 0.2 to 5 mole% of titanium oxide and (iii) at least 91 mole% of silicon oxide and having main peaks at about 26.7° and about 20.9° in its Cu-Kα X-ray diffraction pattern (2θ), a refractive index of 1.53 to B 1.60 and a particle diameter of 0.1 to 1.0 micrometer.

9. The composite material of claim 8 which comprises the spherical particles of the crystalline metal oxide in an amount of 60 to 90% by weight.

* * * * *

UNITED STATES PATENT AND TRADEMARK OFFICE
CERTIFICATE OF CORRECTION

PATENT NO. : 4,591,575
DATED : May 27, 1986
INVENTOR(S) : MINAHIRO OKABAYASHI, ET AL.

It is certified that error appears in the above-identified patent and that said Letters Patent is hereby corrected as shown below:

IN THE CLAIMS

Claim 4, line 7, (column 21, line 55),
  delete "B 1.60", insert --1.60--.

Claim 8, line 9, (column 22, line 60),
  delete "B 1.60", insert --1.60--.

Signed and Sealed this

Twenty-sixth Day of August 1986

[SEAL]

Attest:

DONALD J. QUIGG

Attesting Officer

Commissioner of Patents and Trademarks